(12) United States Patent
Chavez et al.

(10) Patent No.: US 8,043,254 B2
(45) Date of Patent: Oct. 25, 2011

(54) MEDICATION DELIVERY DEVICE

(75) Inventors: Enrico Chavez, Morges (CH); Sandrine Piotelat, Faucigny (FR); Vincent Pongpairochana, La Conversion (CH)

(73) Assignee: Ares Trading SA, Aubonne (CH)

( * ) Notice: Subject to any disclaimer, the term of this patent is extended or adjusted under 35 U.S.C. 154(b) by 796 days.

(21) Appl. No.: 11/884,007

(22) PCT Filed: Jan. 23, 2006
(Under 37 CFR 1.47)

(86) PCT No.: PCT/IB2006/000262
§ 371 (c)(1),
(2), (4) Date: Jun. 20, 2008

(87) PCT Pub. No.: WO2006/085204
PCT Pub. Date: Aug. 17, 2006

(65) Prior Publication Data
US 2009/0198176 A1    Aug. 6, 2009

(30) Foreign Application Priority Data
Feb. 14, 2005   (EP) .................................... 05003110

(51) Int. Cl.
*A61M 31/00* (2006.01)
(52) U.S. Cl. ........................................................ 604/67
(58) Field of Classification Search ............... 604/67
See application file for complete search history.

(56) References Cited

U.S. PATENT DOCUMENTS

| 5,928,197 | A | | 7/1999 | Niehoff et al. |
| 5,928,201 | A | * | 7/1999 | Poulsen et al. ............. 604/208 |
| 6,159,161 | A | | 12/2000 | Hodosh |
| 6,340,357 | B1 | * | 1/2002 | Poulsen et al. ............. 604/208 |
| 6,423,035 | B1 | * | 7/2002 | Das et al. .................... 604/155 |
| 2002/0133113 | A1 | | 9/2002 | Madsen et al. |
| 2002/0151855 | A1 | | 10/2002 | Douglas et al. |
| 2004/0092877 | A1 | | 5/2004 | Langley et al. |

FOREIGN PATENT DOCUMENTS

| DE | 38 24 217 A1 | 1/1990 |
| EP | 1 433 456 A | 6/2004 |
| EP | 1433456 A1 * | 6/2004 |

* cited by examiner

*Primary Examiner* — Nicholas D Lucchesi
*Assistant Examiner* — Jason Flick
(74) *Attorney, Agent, or Firm* — Bacon & Thomas, PLLC

(57) ABSTRACT

The medication delivery device is designed to receive a replaceable medication container (5) and to determine an adjusted medication dose AD for each medication container (5) received if the amount of medication contained in the medication container (5) is not a multiple of a prescribed dose D. The adjusted medication dose is the dose to be delivered instead of the prescribed dose at each use of the medication delivery device with the medication container (5) received. The adjusted dose is determined by selecting one of a first dose, that is higher than the prescribed dose, and of a second dose, that is lower than the prescribed dose, as a function of a variable B that cumulates the values nAD. (AD−D), where nAD is equal to INT (Cont/AD) and Cont is the amount of medication in the medication container received.

15 Claims, 5 Drawing Sheets

Number of cartridges

MEDICATION DELIVERY DEVICE

The present invention relates to a medication delivery device, in particular to an injection device for injecting medication through the skin of a patient.

More specifically, the present invention relates to a device comprising means for receiving a replaceable medication container, such as a cartridge, a control unit and means, controlled by the control unit, for delivering at least one dose of the medication contained in the medication container to a patient. Such a device is disclosed, for example, in US patent application No. 2002/0133113.

A problem with such a known device resides in that the content of the medication container is rarely a multiple of the dose prescribed to the patient, as the dose generally varies from one patient to another and medication containers are standard components. Thus, after all the full doses contained in the medication container have been delivered, there is generally some medication left in the said container. This medication remainder cannot be used and, therefore, is thrown away by the patient with the medication container. This implies that medication is wasted. Over a high number of medication containers used, such a waste may be considerable.

The present invention aims at reducing this medication waste and provides, to this end, a medication delivery device as defined in enclosed claim 1, a method for determining medication doses as defined in enclosed claim 8, and a computer program as defined in enclosed claim 15.

Other features and advantages of the present invention will be apparent from the reading of the following detailed description of preferred embodiments made with reference to the annexed drawings in which.

Figure 1:
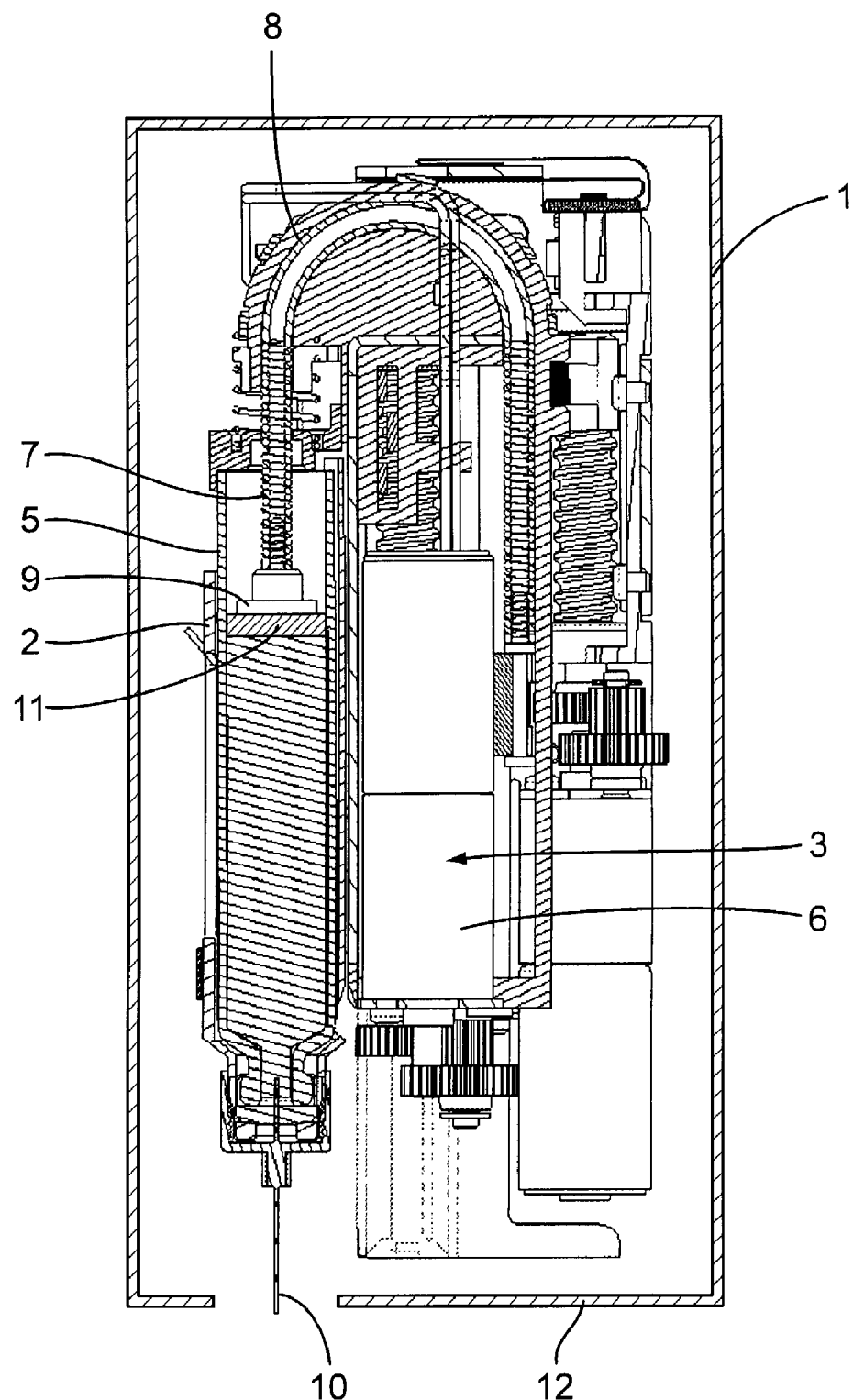
FIG. 1 is a section view of an electronic medication injection device according to the present invention.
Figure 3:
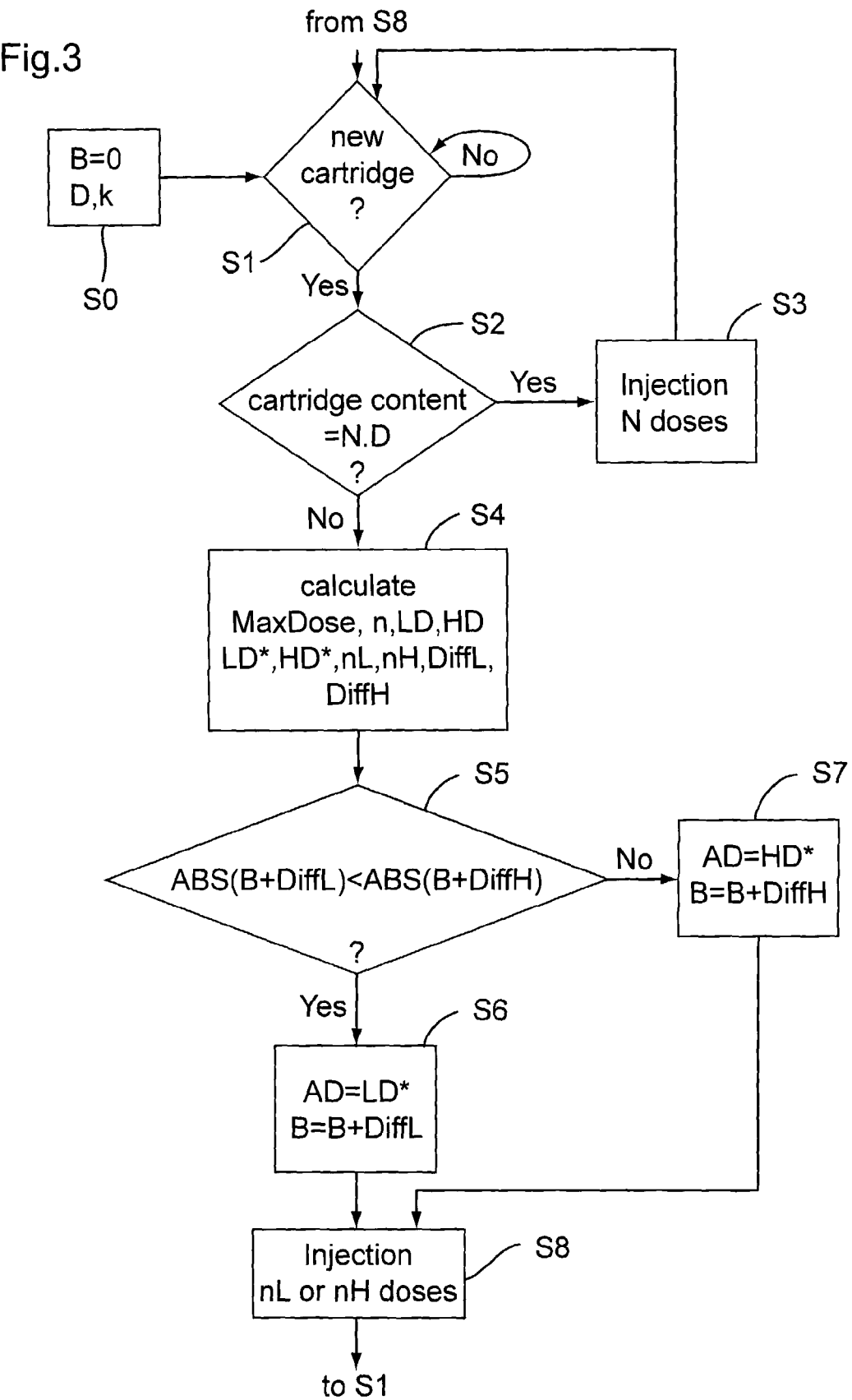
FIG. 3 shows an algorithm performed by the control unit of FIG. 2.
Figure 4:
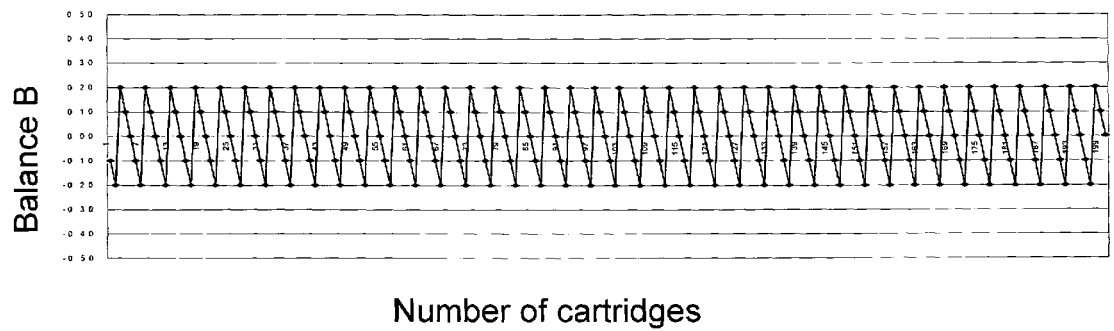
Figure 5:
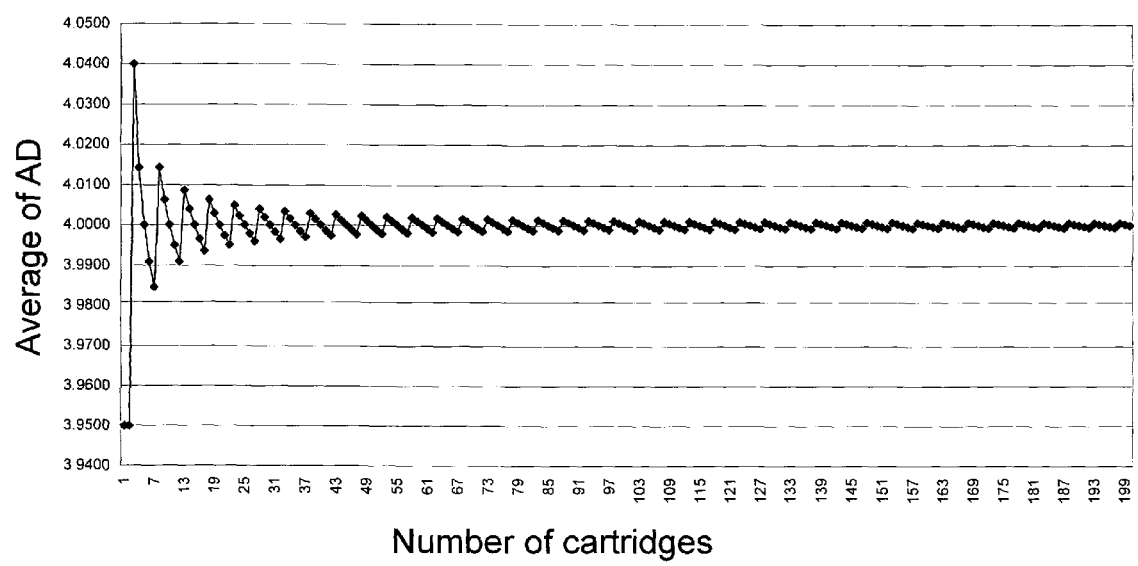

FIGS. 4 and 5 respectively show exemplary curves of a balance B and of an average of adjusted doses AD calculated by the algorithm of FIG. 3 versus a number of cartridges received in the device of FIG. 1.

Figure 2:
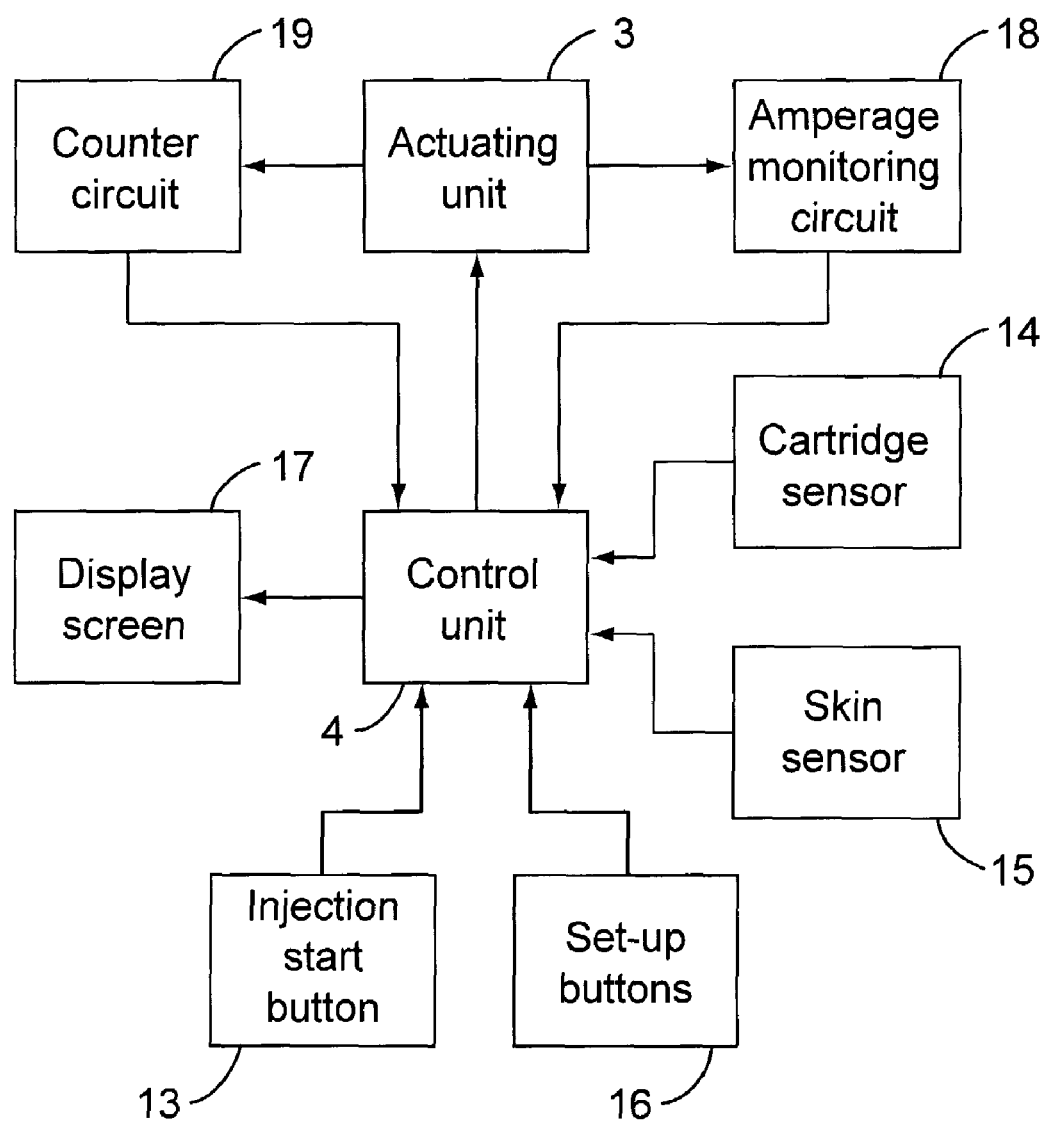
FIG. 2 is a block-diagram showing operation of a control unit for controlling the device of FIG. 1.

Referring to FIGS. 1 and 2, a hand-held electronic injection device according to the invention, for injecting liquid medication through the skin of a patient, comprises a hand-held housing 1 which accommodates a cartridge holder 2, an electromechanical actuating unit 3 and an electronic control unit 4. The cartridge holder 2 is designed to receive a replaceable cartridge 5 containing the liquid medication. The actuating unit 3 comprises an electric motor 6 and a piston rod 7 actuated by the motor 6. The piston rod 7 is in the form of an axially incompressible but laterally elastically deformable tube passing through a curved housing 8 and terminated by a pushing plate 9. After a cartridge 5 has been inserted into the cartridge holder 2 and a needle 10 has been attached to a lower end of the cartridge holder 2 so as to pierce the corresponding end of the cartridge 5, the piston rod 7 is axially displaced by the motor 6 so that the pushing plate 9 comes into contact with a piston 11 in the cartridge 5. Then, if predefined conditions are fulfilled, such as contact of the patient's skin with a bottom surface 12 of housing 1, the piston rod 7 will push the piston 11 to deliver one dose of medication through the needle 10 each time an injection start button 13 is pressed. Once the cartridge 5 is empty, or is considered to be empty, the piston rod 7 is retracted to allow replacement of the cartridge 5.

Referring to FIG. 2, the control unit 4, typically a microprocessor having an internal memory, receives signals from various sensors and buttons on the injection device, and controls the actuating unit 3 according to a program stored in the control unit 4. The sensors may include, in particular, a sensor 14 for detecting the presence of a cartridge 5 in the device and for reading information, such as a bar code, provided on the external wall of cartridge 5, and a sensor 15 for detecting a proximity or a contact of the patient's skin with the bottom surface 12. The buttons include the injection start button 13 and set-up buttons 16. The control unit 4 may also control the display of information for the patient or the physician on a display screen 17 provided on the injection device.

The construction of this medication injection device, in itself, is not part of the invention and, therefore, will not be described in further detail.

In accordance with the present invention, the program stored in the control unit 4 includes a subprogram for adjusting the medication dose to be delivered to the patient in order to reduce medication waste. The algorithm performed by this subprogram is shown in FIG. 3.

This algorithm starts by a step S0 in which a variable B is reset (the function of this variable will be explained later on) and a prescribed dose D, expressed for example in mg, and a predefined constant k, comprised between 0 and 1 and representing a dose accuracy, are stored in the control unit 4. The prescribed dose D and the dose accuracy k are typically provided to the control unit 4 by a physician via the set-up buttons 16.

In a following step S1, it is checked whether a cartridge 5 is inserted in the injection device. If no cartridge is present in the device, the algorithm waits until a cartridge is inserted and then goes to a step S2.

In step S2, it is determined whether the content of the cartridge 5 received in the device, i.e. the initial amount of medication contained in the said cartridge, is a multiple of the prescribed dose, i.e. is equal to the prescribed dose multiplied by an integer number N. The cartridge content is, for example, pre-stored in the control unit 4, provided to the control unit 4 by the patient or the physician via the set-up buttons 16 or read by the sensor 14 on cartridge 5. Alternatively, the cartridge content may be determined by the injection device itself in the following manner: the piston rod 7 is brought into contact with the cartridge piston 11 from its known, retracted position; such a contact, which causes the amperage of motor 6 to increase, is detected by an amperage monitoring circuit 18; a counter circuit 19 counts the number of revolutions of the motor 6 to determine the distance covered by the piston rod 7 from its retracted position up to its contact with the cartridge piston 11, and thus the initial position of the cartridge piston 11 in the cartridge 5; from this initial position and the known dimensions of the cartridge 5, the cartridge content is then determined.

If the answer is yes in step S2, the medication injection can be performed (step S3). The patient will make N injection(s) of the prescribed dose, according to an injection timing prescribed by the physician, and thereafter the control unit 4 will inform the patient, via the display screen 17, that the cartridge 5 is empty and must be replaced. The algorithm will then return to step S1. If the answer is no in step S2, the algorithm goes to a step S4.

In step S4, the following variables are calculated:
$MaxDose = Conc \cdot MaxInjVol$
$n = INT\ (Cont/D)$
$LD = Cont/(n+1)$
$HD = Cont/n$
$LD^* = \max\ (LD, (D - k \cdot D))$ HD*=min (HD, MaxDose, (D+k·D))
nL=INT (Cont/LD*)
nH INT (Cont/HD*)
DiffL=nL·(LD*−D)
DiffH=nH·(HD*−D)
where Conc is the concentration, in mg/ml, of the medication in the cartridge, MaxInjVol is a predetermined constant, expressed in ml, corresponding to the maximum volume that the injection device can inject in one injection, Cont is the aforementioned content, in mg, of the cartridge, INT is the integer part, max is the maximum value and min is the minimum value. The value Conc is for example pre-stored in the control unit 4, provided to the control unit 4 by the patient or the physician via the set-up buttons 16, or read by the sensor 14 on the cartridge 5.

The variables LD and HD represent, respectively, a lower dose and a higher dose than the prescribed dose. Unlike the prescribed dose, these lower and higher doses are dividers of the cartridge content Cont. LD* is a lower dose that is equal to LD if LD is greater than a bottom value (D−k·D) and that is equal to (D−k·D) otherwise. HD* is a higher dose that is equal to HD if HD is smaller than two ceiling values, (D+k·D) and MaxDose, and that is equal to (D+k·D) or MaxDose otherwise. The dose accuracy k is selected by the physician as a function of the disease from which the patient suffers and of the patient himself. The ceiling value MaxDose is a technical restriction of the device.

In a following step S5, it is determined whether the absolute value of (B+DiffL) is smaller than the absolute value of (B+DiffH). If the answer is yes, an adjusted dose AD corresponding to the cartridge 5 inserted in the injection device is equal to the lower dose LD*, and the variable B is given the new value (B+DiffL) (step S6). If the answer is no, the adjusted dose AD is equal to the higher dose HD*, and the variable B is given the new value (B+DiffH) (step S7). This adjusted dose AD will be the dose to be injected into the patient instead of the prescribed dose D at each injection with the cartridge 5 inserted in the device.

The medication injection can then be performed (step S8). The patient will make nL (if LD* is selected as the adjusted dose) or nH (if HD* is selected as the adjusted dose) injections of the adjusted dose according to the injection timing prescribed by the physician. After these nL or nH injections, the patient will be informed by the display screen 17 that the cartridge must be replaced and the algorithm will return to step S1.

Steps S1 to S8 are carried out for each cartridge inserted in the injection device. So long as the prescribed dose remains unchanged, the variable B is not reset, even if the injection device is switched off between two injections. If, at any moment, the prescribed dose stored in the device is changed, the algorithm goes to step S0 where the variable B is reset.

The variable B represents a balance that cumulates the values nAD. (AD−D), where nAD is equal to INT (Cont/AD), as different cartridges are successively used in the device. In other words, the variable B represents the difference, at a given instant, between the amount of medication administered to the patient and the amount of medication that would have been administered if the dose had not been changed with respect to that prescribed. Such a difference may be positive or negative.

It can be readily derived from the above that if, for each cartridge used, the adjusted dose is equal to LD or HD, medication waste is eliminated. If, on the other hand, the adjusted dose is equal to a ceiling value, (D+k·D) or MaxDose, or to the bottom value (D−k·D) for at least one of the cartridges used, with k being different from zero and MaxDose being different from HD, then medication waste is not eliminated but is at least statistically reduced, i.e. reduced over a large number of cartridges used, as will be explained later on.

One will further note that the decision rule used in step S5, involving the variable B, guarantees that the average of the adjusted doses as a function of the number of cartridges used converges to the prescribed dose, i.e. that after a certain number of cartridges have been used, the average of the adjusted doses delivered to the patient is substantially equal to the prescribed dose. In many medical treatments indeed, such as the treatment of growth deficiency, the dose administered at each injection need not accurately correspond to that prescribed by the physician, provided that the average of the administered doses over a certain period, typically one or several weeks, is substantially equal to the prescribed dose. The present invention uses this medical tolerance to reduce medication waste.

Although the decision rule used in step S5 is considered by the present inventors as being optimal for the rate of convergence of the average adjusted dose to the prescribed dose, it must be noted that other decision rules involving the variable B could be chosen. In a variant of the present invention, the lower dose LD* is selected as the adjusted dose if the value of variable B is positive and the higher dose HD* is selected as the adjusted dose if the value of variable B is negative or zero.

Another property of the above algorithm is that the absolute value of the variable B is never greater than 50% of the prescribed dose. Thus, the variation between the amount of medication received by the patient and the amount of medication that he/she should have received according to his/her medical prescription remains at any time limited.

As already mentioned, with the algorithm according to the present invention, medication waste is at least statistically reduced. Simulations carried out by the present inventors, by varying the prescribed dose from 0.01 to MaxDose and the dose accuracy from 0 to 0.5, have revealed, in particular, that as of 24 cartridges used:

the medication waste W(AD) obtained when the doses administered are adjusted doses each equal to one of the aforementioned ceiling and bottom values, is, in more than 90% of the cases, lower than the medication waste W(D) obtained when the dose administered is constantly equal to the prescribed dose, the medication waste W(AD) is always lower than W(D)+1%, and the absolute value of the difference between the average adjusted dose and the prescribed dose is not greater than 2% of the prescribed dose, it being specified that the medication waste is defined as follows:

$$W = \frac{\sum_i r_i}{\sum_i Cont_i}$$

where $r_i$ is the medication remainder in a given cartridge i after all full doses contained in this cartridge have been injected, and $Cont_i$ is the content of cartridge i. Other results of the above-mentioned simulations are that, as of 100 cartridges used, the medication waste W(AD) is always lower than W(D)+0.2%, and that, as of 200 cartridges used, the medication waste W(AD) is always lower than W(D)+0.1%.

In a variant of the present invention, which may be applied to cases where the physician allows a larger variation between the injected doses and the prescribed dose, and where no technical restriction exists as to the volume of medication that can be injected by the device in one injection, the ceiling variable MaxDose and the dose accuracy k are suppressed from the algorithm. Medication waste is, in this variant, always zero.

By way of illustration of the present invention, a numerical example of performing the algorithm shown in FIG. 3 is given herebelow:

Content of each cartridge (Cont)=7.9 mg
Prescribed dose (D)=4 mg
Dose accuracy (k)=0.1 (10%)
Number (n) of full doses (D) in each cartridge=INT (Cont/D)=1
MaxDose=5.8 mg/ml×0.8 ml=4.6 mg
LD=Cont/(n+1)=3.95 mg
D−k·D=4−0.4=3.6 mg
LD*=LD=3.95 mg
HD=Cont/n=7.9 mg
HD*=D+k·D=4.4 mg FIGS. 4 and 5 respectively show the curves of the balance B and the average of the adjusted doses as a function of the number of cartridges used.

The present invention has been described above in the context of an injection device for injecting medication through the skin of a patient. However, it is clearly apparent that the invention may apply to other medication delivery devices, for example to devices which provide the patient with appropriate doses of medication to be administered orally.

The invention claimed is:

1. A medication delivery device comprising means for receiving a replaceable medication container, a control unit and means, controlled by said control unit, for delivering at least one dose of the medication contained in said medication container to a patient, wherein said control unit comprises means for determining an adjusted medication dose AD for each medication container received in the medication delivery device if the amount of medication contained in said medication container received is not a multiple of a prescribed dose D, said adjusted medication dose being the dose to be delivered by said delivering means instead of the prescribed dose at each use of the medication delivery device with said medication container received, said adjusted dose being determined by selecting one of a first dose, that is higher than the prescribed dose, and of a second dose, that is lower than the prescribed dose, as a function of a variable B that cumulates the values nAD. (AD−D), where nAD is equal to INT (Cont/AD) and Cont is the amount of medication in said medication container received.

2. A medication delivery device according to claim 1, wherein the adjusted dose is the one, among the first and second doses, for which the absolute value of the variable B is lower.

3. A medication delivery device according to claim 1, wherein the adjusted dose is equal to the first dose if the variable B is negative and is equal to the second dose if the variable B is positive.

4. A medication delivery device according to claim 1, wherein the first dose is equal to (Cont/n) and the second dose is equal to (Cont/(n+D), where n is equal to INT (Cont/D).

5. A medication delivery device according to claim 1, wherein the first dose is equal to the minimum of (Cont/n) and at least one ceiling value and the second dose is equal to the maximum of (Cont/(n+1)) and at least one bottom value.

6. A medication delivery device according to claim 5, wherein said at least one ceiling value includes the value (D+k·D) and said at least one bottom value includes the value (D−k·D), where k is a predefined constant between 0 and 1.

7. A medication delivery device according to claim 1, arranged in the form of an electronic injection device adapted to inject medication through the skin of a patient.

8. A method for determining medication doses, said method being performed by a control unit in a medication delivery device also comprising means for receiving a replaceable medication container and means, controlled by said control unit, for delivering at least one dose of medication contained in said medication container to a patient, comprising the steps: determining an adjusted medication dose AD for each medication container received in the medication delivery device if the amount of medication contained in said medication container received is not a multiple of a prescribed dose D, said adjusted medication dose being the dose to be delivered by said delivering means instead of the prescribed dose at each use of the medication delivery device with said medication container received, said adjusted dose being determined by selecting one of a first dose, that is higher than the prescribed dose, and of a second dose, that is lower than the prescribed dose, as a function of a variable B that cumulates the values nAD. (AD−D), where nAD is equal to INT (Cont/AD) and Cont is the amount of medication in said medication container received.

9. A method according to claim 8, wherein the adjusted dose is the one, among the first and second doses, for which the absolute value of the variable B is lower.

10. A method according to claim 8, wherein the adjusted dose is equal to the first dose if the variable B is negative and is equal to the second dose if the variable B is positive.

11. A method according to claim 8, wherein the first dose is equal to (Cont/n) and the second dose is equal to (Cont/(n+1)), where n is equal to INT (Cont/D).

12. A method according to claim 8, wherein the first dose is equal to the minimum of (Cont/n) and at least one ceiling value and the second dose is equal to the maximum of (Cont/(n+1)) and at least one bottom value.

13. A method according to claim 12, wherein said at least one ceiling value includes the value (D+k·D) and said at least one bottom value includes the value (D−k·D), where k is a predefined constant between 0 and 1.

14. A method according to claim 8, wherein the amount of medication contained in said medication container is determined by bringing a piston rod of said delivering means into contact with a piston of said medication container from a known, retracted position; detecting said contact by monitoring the amperage of an electric motor of said delivering means which drives said piston rod; counting the number of revolutions of said electric motor to determine the distance covered by said piston rod from its retracted position up to its contact with said piston, and thus the position of said piston in said medication container; and determining the amount of medication contained in said medication container from said position of said piston.

15. A computer program executable by a control unit in a medication delivery device also comprising means for receiving a replaceable medication container and means, controlled by said control unit, for delivering at least one dose of medication contained in said medication container to a patient, comprising an instructions code for performing the method defined in claim 8.

* * * * *